United States Patent [19]

Kogure et al.

[11] Patent Number: 4,835,155
[45] Date of Patent: May 30, 1989

[54] PROCESS FOR PROTECTION OF BRAIN CELLS

[75] Inventors: Kyuya Kogure, Shakujii; Mitsuo Masaki, Chiba, both of Japan

[73] Assignee: Nippon Chemiphar Co., Ltd., Tokyo, Japan

[21] Appl. No.: 87,408

[22] Filed: Aug. 20, 1987

[30] Foreign Application Priority Data

Aug. 20, 1986 [JP] Japan ................... 61-194925

[51] Int. Cl.$^4$ ........................... A61K 31/495
[52] U.S. Cl. ................................. 514/255
[58] Field of Search ........................ 514/255

[56] References Cited

U.S. PATENT DOCUMENTS 4,528,194 7/1985 Masaki ................. 514/255

OTHER PUBLICATIONS

*Delayed Neuronal Death in the Gerbil Hippocampus Following Ischemia*, Brian Research, Kirino, 1982, vol. 239, pp. 57-69.
*Selective Vulnerability of the Hippocampus to Ischemic*, Progress in Brain Research, Kirino et al., vol. 63, pp. 39-58.
Chemical Abstracts, vol. 99, 1983, p. 622.

Primary Examiner—Stanley J. Friedman
Attorney, Agent, or Firm—Gerald J. Ferguson, Jr.

[57] ABSTRACT

A process for protection of brain cells comprises orally or parenterally administering into a man suffering from ischemia or being susceptable to ischemia a piperazine derivative having the formula:

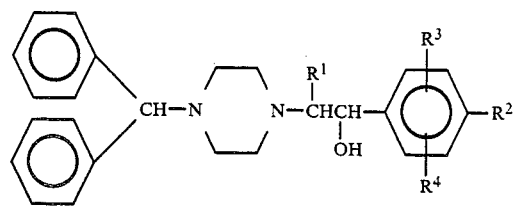

wherein $R^1$ is hydrogen or a lower alkyl group, $R^2$ is hydroxyl, an aralkyloxy group, a lower alkoxy group having 1-5 carbon atoms or a lower alkenyloxy group having 3-5 carbon atoms, $R^3$ is hydrogen, an aralkyloxy group, a lower alkoxy group having 1-5 carbon atoms or a lower alkenyloxy group having 3-5 carbon atoms and $R^4$ is hydrogen or a lower alkoxy group having 1-5 carbon atoms.

6 Claims, No Drawings

PROCESS FOR PROTECTION OF BRAIN CELLS

BACKGROUND OF THE INVENTION

1. Field of the Invention

The present invention relates to a process for protection of brain cells.

2. Description of Prior Art

Recently, since a first aid treatment system has progressed, rate of death caused by cerebral infarction or cerebral hemorrhage is reduced. However, the reduced rate of death brings about another problem in that the cerebral infarction or cerebral hemorrhage causes dementia as an after effect. It is known that the cerebrovascular dementia is brought about through damage of brain cells which takes place in the course of ischemia caused by cerebral infarction or cerebral hemorrhage.

It has been recently confirmed that the damage of cells (or degeneration of brain cells) is caused not only as a direct result of the ischemia (that is, ischemic cell change), but also by a delayed effect (i.e., delayed neuronal death) which is observed even after the blood flow is recovered. Kirino et al. have reported in Brain Res. 239: 57–69 (1982) that when meriones unguiculatus is treated to ischemia for a short time at the forebrain and the blood flow is recovered, pyramidal cells are damaged and lost in the CA1 area of hippocampus after lapse of a certain period. This means that the brief ischemia causes the delayed neuronal damage. The hippocampus is the area of a brain where intellectual activity relating to emotion and memory is controlled. Accordingly, it is considered that damage of hippocampus is one reason to cause dementia.

Therefore, it has been earnestly desired to prevent or treat the dementia which may be observed after cerebral infarction and cerebral hemorrhage.

Regarding the above subject, Kirino et al. have further reported in Progress in Brain Research, vol. 63: 39–58 (1985) that pentobarbital having a cell membrane-stabilizing effect shows an effect of protection of brain cells and serves to markedly suppress the above-mentioned delayed neuronal damage.

As is described above, pentobarbital is of value for subsiding the delayed neuronal damage. However, since pentobarbital acts nonselectively and the action of central nervous system is also strongly subsided, pentobarbital cannot be used in practice as a brain cell protective agent.

SUMMARY OF THE INVENTION

The present inventors have made study for a compound showing an effective brain cell protective action and now discovered that a piperazine derivative having the formula (I):

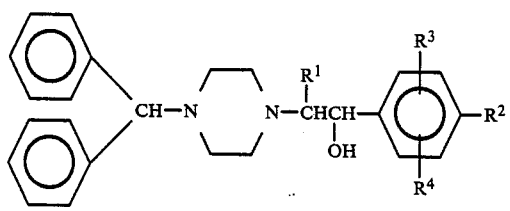

wherein $R^1$ is hydrogen or a lower alkyl group, $R^2$ is hydroxyl, an aralkyloxy group, a lower alkoxy group having 1–5 carbon atoms or a lower alkenyloxy group having 3–5 carbon atoms, $R^3$ is hydrogen, an aralkyloxy group, a lower alkoxy group having 1–5 carbon atoms or a lower alkenyloxy group having 3–5 carbon atoms and $R^4$ is hydrogen or a lower alkoxy group having 1–5 carbon atoms. shows a selective brain cell protective action.

DETAILED DESCRIPTION OF THE INVENTION

The piperazine derivative of the formula (I) is already known to serve as an effective brain circulation improving agent, having an effect of increasing the blood stream by peripheral vasodilation, more particularly, vertebral artery and an effect of inhibition of platelet aggregation (Japanese Patent Provisional Publications No. 58(1983)-124776 and No. 59(1984)-101475).

In piperazine derivatives having the formula (I), examples of the lower alkyl group for $R^1$ include methyl, ethyl, n-propyl and isopropyl. Examples of the lower alkoxy group for $R^2$, $R^3$ and $R^4$ include methoxy, ethoxy and n-propyloxy. Examples of the lower alkenyloxy group for $R^2$ and $R^3$ include propenyloxy, isopropenyloxy and allyloxy. Examples of the aralkyloxy group for $R^2$, and $R^3$ include benzyloxy, phenethyloxy and p-methoxybenzyloxy.

The piperazine derivative of the formula (I) can be in the form of a salt with a pharmaceutically acceptable acid. Such acid can be hydrochloric acid, sulfuric acid, tartaric acid, fumaric acid, maleic acid, p-toluenesulfonic acid and methanesulfonic acid.

The piperazine derivative of the formula (I) can be prepared, for instance, by reducing a carbonyl compound of the formula (II) according to the following equation:

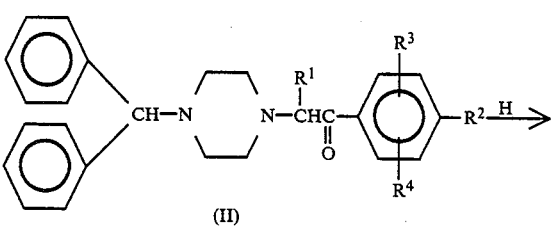

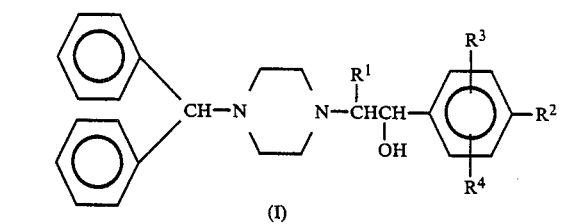

(In the equation, $R^1$, $R^2$, $R^3$ and $R^4$ have the same meanings as above.).

Representative examples of the piperazine derivatives of the formula (I) which serve as the active components in the pharmaceutical composition of the present invention include the following compounds:

Compound 1: 1-(4-benzyloxyphenyl)-2-(4-diphenylmethylpiperazinyl)ethanol monohydrochloride Compound 2: 1-(2,4-dibenzyloxyphenyl)-2-(4-diphenylmethylpiperazinyl)ethanol mono-hydrochloride Compound 3: dl-threo-1-(4-benzyloxyphenyl)-2-(4-diphenylmethylpiperazinyl)propanol dihydrochloride Compound 4: 1-(2,4-dimethoxyphenyl)-2-(4-diphenylmethylpiperazinyl)ethanol dihydrochloride
Compound 5: 1-(3,4-dimethoxyphenyl)-2-(4-diphenylmethylpiperazinyl)ethanol dihydrochloride
Compound 6: 2-(4-diphenylmethylpiperazinyl)-1-(2,3,4-trimethoxyphenyl)ethanol dihydrochloride
Compound 7: 2-(4-diphenylmethylpiperazinyl)-1-(3,4,5-triemthoxyphenyl)ethanol monohydrochloride
Compound 8: 1-(4-allyloxyphenyl)-2-(4-diphenylmethylpiperazinyl)ethanol monohydrochloride
Compound 9: 1-(2-allyloxy-4-methoxyphenyl)-2-(4-diphenylmethylpiperazinyl)ethanol dihydrochloride
Compound 10: 2-(4-diphenylmethylpiperazinyl)-1-(4-hydroxyphenyl)ethanol monohydrochloride
Compound 11: dl-erythro-2-(4-diphenylmethylpiperazinyl)-1-(4-hydroxyphenyl)propanol ½ tartarate
Compound 12: dl-threo-2-(4-diphenylmethylpiperazinyl)-1-(4-hydroxyphenyl)propanol tartarate Other valuable compounds having the formula (I) can be prepared in the manner described in the aforementioned Japanese Patent Provisional Publications No. 58(1983)-124776 and No. 59(1984)-101475.

The pharmacological effect of reducing the delayed neuronal damage or death which is provided by the active component of the formula (I) is shown by the following results of the pharmacological experiments in which the test compound was administered into a greater circulation system. Results of toxicity tests are also given.

RESTRAINT EFFECT ON DELAYED NERVE CELL AFFECTION

Procedure of Experiment

A male meriones unguiculatus (approx. 12–16 week ages) was anesthetized. Its bilateral common carotid arteries at the neck was exposed, and occluded with clips for 5 minutes to cause ischemia at its forebrains. At the same time when the blood flow was recovered, 1-(3,4-dimethoxyphenyl)-2-(4-diphenylmethylpiperazinyl)ethanol dihydrochloride (hereinafter referred to as "Medicament A") or 0.2% methylcellulose (which was employed as vehicle for the above test compound) was administered intraperitoneally at a dose of 30 mg/kg (n=10) for each.

After seven days, the treated animal was fixed by perfusion fixation which was carried out by introducing approx. 300 ml of 10% aqueous formalin solution into left ventricle at 120 cm·H$_2$O, and were decapitated. After decapitated portion was left at room temperature for one hour, the brain was taken out and immersed into the same solution for 48 hours. After the brains were dissected out and cut coronally into small blocks, the blocks were dehydrated and then embedded in paraffin according to the conventional manner. From the blocks, coronary slices of 5 μm thick perpendicularly to the long axis of brain was taken out at 2 mm posterior to the bregma. The specimen was then dyed by Nissle dyeing method.

Similar specimen was also taken out of a normal group consisting of six animals which had not been subjected to the treatment for causing ischemia.

The specimen was observed by means of an optical microscope to measure number of well-shaped pyramidal cells (i.e., neurons) contained in CA1 area of the specimen, and was photographed to measure the length of the pyramidal cell layer in the area. Then, number of pyramidal cells per 1 mm was calculated and studied.

Experimental Result

Microscopic observation with low enlargement taught that the dyeing of pyramidal cells of the CA1 area was kept as equally as that of the other area in the normal group. Also, microscopic observation with high enlargement taught that the shapes of cells were kept well. In the group to which 30 mg/kg of Medicament A had been administered, almost the same histological image as that of the normal group is recognized. Both microscopic observations with low and high enlargement gave the same result as that of the experiment of the normal group, meaning that the cells remained alive.

In the vehicle administered group for control, cells changed into irreversible degeneracy, meaning fusion necrocytosis. The analysis of number of the cells in 1 mm of pyramidal cells layer in CA1 area of each group taught that lapse of cells were restrained in the group to which 30 mg/kg of Component A had been administered, as compared with those of the vehicle administered group. It apparently indicates effectiveness of the medicament (Table 1). Additionally, it was recognized the number of cells tended to decrease in the vehicle administered group, as compared with that in the normal control group. However, no statistically significant difference on the number of cells was detected between those groups, and cells obstruction was restrained.

TABLE 1

| Specimen | Number of CA1 neurons (/mm) |
| --- | --- |
| Normal Group (n = 6) | 66.03 ± 7.37 |
| Medicament A (n = 10) | 47.16 ± 4.31 |
| Vehicle | 7.51 ± 3.26 |

ACUTE TOXICITY

The ddN male mouse having a weight of about 20 g was administered orally with the active component of the present invention, and was observed for seven days. The experimental result is shown in Table 2.

TABLE 2

| Active Component | LD$_{50}$ (mg/kg) |
| --- | --- |
| A | 470 |
| B | more than 2,000 |
| C | more than 2,000 |

A: 1-(3,4-dimethoxyphenyl)-2-(4-diphenylmethylpiperazinyl)ethanol dihydrochloride
B: 2-(4-diphenylmethylpiperazinyl)-1-(3,4,5-trimethoxyphenyl)ethanol monohydrochloride
C: 2-(4-diphenylmethylpiperazinyl)-1-(4-hydroxyphenyl)ethanol monohydrochloride The above pharmacological experiments have revealed that piperazine derivatives having the formula (I) show a brain cell protective action similar to that of pentobarbital, and that the derivatives are highly safe medicaments.

Further, piperazine derivative of the formula (I) show essentially no anesthetic action, so long as they are administered at an ordinary dose level. Accordingly, piperazine derivatives of the formula (I) are effective to greatly reduce delayed neuronal damage which is sometimes caused by cerebral infarction or cerebral hemorrhage, particularly for aged patients. Thus, piperazine derivatives of the formula (I) are effective to prevent dementia.

Further, the piperazine derivatives of the formula (I) can be employed for obviating after-effect caused by temporary ischemia which may be brought about by temporary blood pressure reduction due to drowning, accident in anesthetic treatment, external wound, drugs, and the like.

Generally, it is known that a drug for treatment of brain should be passed through blood-brain barrier (BBB). It is understood that the piperazine derivatives of the formula (I) easily pass through BBB because they are effective through the administration into the greater circularion system.

Accordingly, the active components of the invention, namely, piperazine derivatives of the formula (I) can be administered through ordinary routes such as by oral administration and parenteral administration using a suppository or an injection.

Examples of the preparation forms for oral administration include tablets, capsules, powder, granules, and syrup. Examples of the preparation forms for parenteral administration include suppository and injection. In the formulation of these preparations, there can be used excipients, disintegrants, binders, lubricants, pigments, diluents and the like which are commonly used in the art. Examples of the excipients include glucose, lactose and microcrystalline cellulose. Examples of the disintegrants include starch and carboxymethylcellulose calcium. Examples of the lubricants include magnesium stearate and talc. Examples of the binders include hydroxypropylcellulose, gelatin and polyvinylpyrrolidone.

The does for injection generally is in the range of approx. 0.1 mg to 100 mg/day, preferably approx. 0.5 mg to 100 mg/day, for an adult. The dose for oral administration generally is in the range of approx. 1 mg to 1,000 mg/day, preferably approx. 5 mg to 1,000 mg/day, for an adult. These values are represented in terms of the amount of the physiologically active compound, namely the piperazine derivative of the formula (I). These doses can be either increased or decreased depending upon the age and conditions of the patients.

The following examples further describe the present invention.

REFERENCE EXAMPLE 1

2-(4-Diphenylmethylpiperazinyl)-1-(2,3,4-trimethoxyphenyl)ethanol

In a mixture of 100 ml of ethanol and 30 ml of chloroform was dissolved 13.8 g (30 mmol) of 2-(4-diphenylmethylpiperazinyl)-1-(2,3,4-trimethoxyphenyl)etha and to the resulting solution under chIling with ice was added 2.27 g (60 mmol) of sodium borohydride over 20 minutes. The solution was stirred for two hours at room temperature, and then 50 ml of saturated aqueous ammonium chloride solution and 100 ml of water were added. The obtained solution was extracted with 200 ml of ethyl acetate. The organic layer was washed successively with water and saturated saline and was drived over anhydrous sodium sulfate. The solvent was distilled off, and residue was recrystallized from chloroform-ethanol to give 9.70 g of 2-(4-diphenylmethylpiperazinyl)-1-(2,3,4-trimethoxyphenyl)ethanol as a white crystalline product (yield: 70%). m.p. 128° C.

$IR\nu_{max}^{KBr}$: 3420, 2940, 2805, 1600, 1485, 1460, 1420, 1270, 1140, 1100, 1020, 1000, 745, 700 cm$^{-1}$.

NMR spectrum (CDCl$_3$) δ: 2.2–3.0 (10H, m,

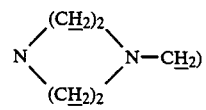

3.90 (3H, s, OCH$_3$), 3.92 (3H, s, OCH$_3$), 3.94 (3H, s, OCH$_3$), 4.21 (1H, s, Ph$_2$CH), 4.94 (1H, dd, J=8Hz, J=4Hz, CH—OH), 6.5–7.5 (12H, m, aromatic hydrogen).

| Analysis (C$_{28}$H$_{34}$N$_2$O$_4$) | | | |
|---|---|---|---|
| | C | H | N |
| Calculated (%) | 72.70 | 7.41 | 6.06 |
| Found (%) | 72.48 | 7.60 | 5.86 |

In 23 ml of acetone was dissolved 2.31 g. (5 m.mol) of the above free base under heating. To the solution was added 10 ml of 1-N HCl in acetone to give 2.19 g of 2-(4-diphenylmethylpiperazinyl)-1-(2,3,4-trimethoxyphenyl)ethanol dihydrochloride as a white crystalline powder (yield 82%). m.p. 189° C. (decomposed)

$IR\nu_{max}^{KBr}$: 3250, 2940, 2420, 1600, 1490, 1450, 1420, 1280, 1195, 1095, 1015, 750, 710 cm$^{-1}$.

REFERENCE EXAMPLE 2

1-(3,4-Dimethoxyphenyl)-2-(4-diphenylmethylpiperazinyl)ethanol 1-(3,4-Dimethoxyphenyl)-2-(4-diphenylmethylpiperazinyl)ethanone was treated in the same manner as in Reference Example 1. The resulting product was purified by silica gel column chromatography and then recrystallized from ether to give 1-(3,4-dimethoxyphenyl)-2-(4-diphenylmethylpiperazinyl)ethanol (yield 75%). m.p. 85° C.

$IR\nu_{max}^{KBr}$: 3400, 2820, 1600, 1510, 1450, 1265, 1235, 1140, 1030, 860, 760, 705 cm$^{-1}$.

NMR spectrum (CDCl$_3$) δ: 2.2–2.9 (10H, m,

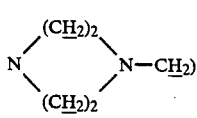

3.83 (3H, s, OCH$_3$), 3.86 (3H, s, OCH$_3$), 4.21 (1H, s, Ph$_2$CH), 4.61 (1H, t, J=7Hz, CHOH), 6.7–7.5 (13H, m, aromatic hydrogen).

| Analysis (C$_{27}$H$_{32}$N$_2$O$_3$) | | | |
|---|---|---|---|
| | C | H | N |
| Calculated (%) | 74.97 | 7.46 | 6.48 |
| Found (%) | 75.19 | 7.62 | 6.68 |

The above-mentioned free base was converted into its hydrochloride in the same manner as in Reference Example 1 and recrystallized from ethanol-ether to give 1-(3,4-dimethoxyphenylmethylpiperazinyl)ethanol dihydrochloride (yield 74%). m.p. 175° C. (decomposed)

$IR\nu_{max}^{KBr}$: 3360, 2950, 2550, 1600, 1505, 1450, 1260, 1230, 1160, 1140, 1020, 755, 700 cm$^{-1}$.

EXAMPLE 1

Preparation Example (Pellets)

One pellet (220 mg) contained the following components:

| | |
|---|---|
| Active component | 50 mg |
| Lactose | 100 mg |
| Starch | 50 mg |
| Magnesium stearate | 5 mg |
| Hydroxypropylcellulose | 15 mg |

EXAMPLE 2

Preparation Example (Capsules)

One capsule contained 350 mg of the following components:

| | |
|---|---|
| Active component | 40 mg |
| Lactose | 200 mg |
| Starch | 70 mg |
| Polyvinylpyrrolidone | 5 mg |
| Crystalline cellulose | 35 mg |

EXAMPLE 3

Preparation Example (Granules)

The granules contained the following components per 1 g:

| | |
|---|---|
| Active component | 200 mg |
| Lactose | 450 mg |
| Corn starch | 300 mg |
| Hydoxypropylcellulose | 50 mg |

EXAMPLE 4

Preparation Example (Injection)

In approx. 600 ml of distilled water were dissolved under stirring 2.5 g of the active component and 3.5 g of D-mannitol. To the resulting solution was added phosphate buffer to adjust the pH value of the solution to 4.0–5.5. Distilled water was added to the solution so as to make 1,000 ml solution. The solution was then filtered and charged into ampules in an amount of 4 ml per each ampule in the conventional manner.

EXAMPLE 5

Preparation Example (Injection)

The 1,000 ml solution prepared and filtered in the same manner as in Example 4 was charged into vials and freeze-dried in the conventional manner.

EXAMPLE 6

Preparation Example (Injection)

In approx. 660 ml of distilled water were dissolved under stirring 0.3 g of the active component and 8.7 g of NaCl. To the resulting solution was added phosphate buffer to adjust the pH value of the solution to 4.0–5.5. Distilled water was added to the solution so as to make 1,000 ml solution. The solution was then filtered and charged into ampules.

EXAMPLE 7

Preparation Example (Injection)

The 1,000 ml solution prepared and filtered in the same manner as in Example 6 was charged into vials and freeze-dried in the conventional manner.

We claim:

1. A process for reducing delayed neuronal damage or death which occurs as a result of ischemia in the brain comprising; administering into a man suffering from ischemia or being susceptible to ischemia a piperazine derivative having the formula:

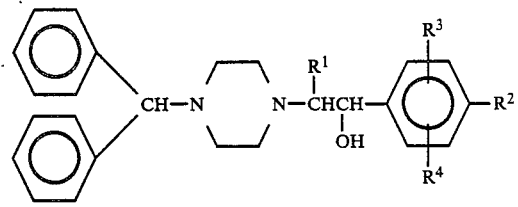

wherein $R^1$ is hydrogen or a lower alkyl group, $R^2$ is hydroxyl, an aralkyloxy group, a lower alkoxy group having 1–5 carbon atoms or a lower alkenyloxy group having 3–5 carbon atoms, $R^3$ is hydrogen, an aralkyloxy group, a lower alkoxy group having 1–5 carbon atoms or a lower alkenyloxy group having 3–5 carbon atoms, and $R^4$ is hydrogen or a lower alkoxy group having 1–5 carbon atoms.

2. The process as claimed in claim 1, wherein the piperazine derivative is 1-(3,4-dimethoxy phenyl)-2-(4-diphenylmethylpiperazinyl)ethanol.

3. The process as claimed in claim 1, wherein the piperazine derivative is in the form of a salt with a pharmaceutically acceptable acid.

4. The process as claimed in claim 1, wherein the piperazine derivative is administered in the form of pellets, capsules, granules or injection.

5. The process as claimed in claim 1, wherein the piperazine derivative is parenterally administered at a dose of 0.1 to 100 mg per day.

6. The process as claimed in claim 1, wherein the piperazine derivative is orally administered at a dose of 1 to 1,000 mg per day.

* * * * *